United States Patent [19]

Hood, Jr.

[11] Patent Number: 4,501,280
[45] Date of Patent: Feb. 26, 1985

[54] AUTOMATIC IDENTIFICATION OF CUFF SIZE IN AUTOMATED BLOOD PRESSURE MONITORS

[75] Inventor: Rush W. Hood, Jr., Tampa, Fla.

[73] Assignee: Critikon, Inc., Tampa, Fla.

[21] Appl. No.: 482,664

[22] Filed: Apr. 6, 1983

[51] Int. Cl.³ .............................................. A61B 5/02
[52] U.S. Cl. .................................... 128/677; 128/686
[58] Field of Search ....................... 128/677, 680-683, 128/686

[56] References Cited

U.S. PATENT DOCUMENTS

| | | | |
|---|---|---|---|
| 4,210,154 | 7/1980 | Klein | 128/686 X |
| 4,263,918 | 4/1981 | Swearingen et al. | 128/681 |
| 4,321,929 | 3/1982 | Lemelson et al. | 128/680 X |
| 4,349,034 | 9/1982 | Ramsey | 128/681 |
| 4,360,029 | 11/1982 | Ramsey | 128/681 |
| 4,429,699 | 2/1984 | Hatschek | 128/686 X |

FOREIGN PATENT DOCUMENTS 2069706  8/1981  United Kingdom ................ 128/682

OTHER PUBLICATIONS

Deitenbeck; "Unique Noninvasive Technique for Measuring BP of the Neonate"; Med. Instr., vol. 11, No. 1, Jan.-Feb., 1977, pp. 54-55.
Barnick et al.; "Instrument for Measuring BP of Newborn Infants", vol. 12, No. 3; Biomed. Engr., May-Jun., 1978, pp. 171-173.

Primary Examiner—Lee S. Cohen
Assistant Examiner—Angela D. Sykes
Attorney, Agent, or Firm—Audley A. Ciamporcero, Jr.

[57] ABSTRACT

Automated blood pressure monitors utilizing a pressurized cuff are adapted automatically to work with a variety of cuff sizes, including neonatal. An acoustical pressure pulse is generated at the monitor, propagated to and through the cuff, and back to a pressure transducer in the monitor. The total time of propagation is indicative of the cuff size being utilized.

3 Claims, 7 Drawing Figures

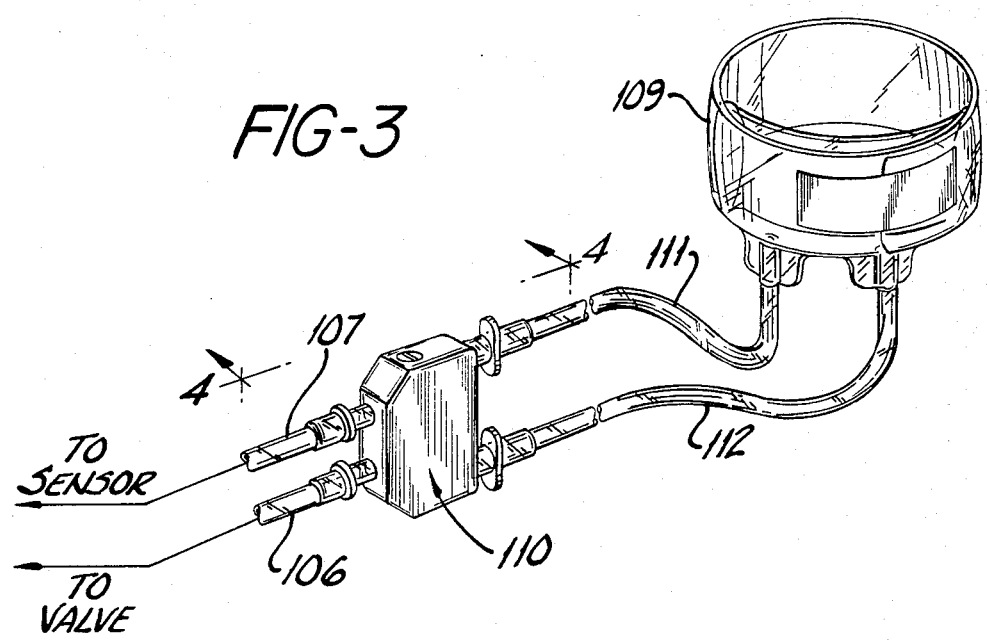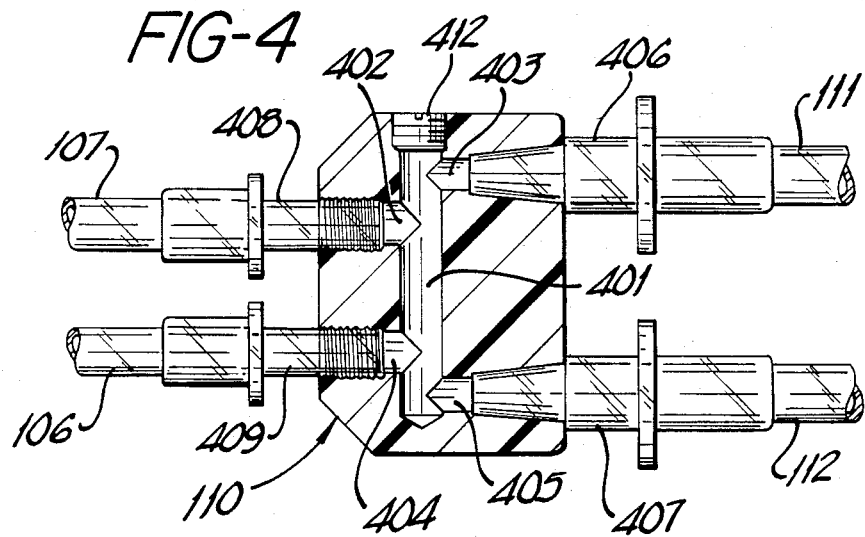

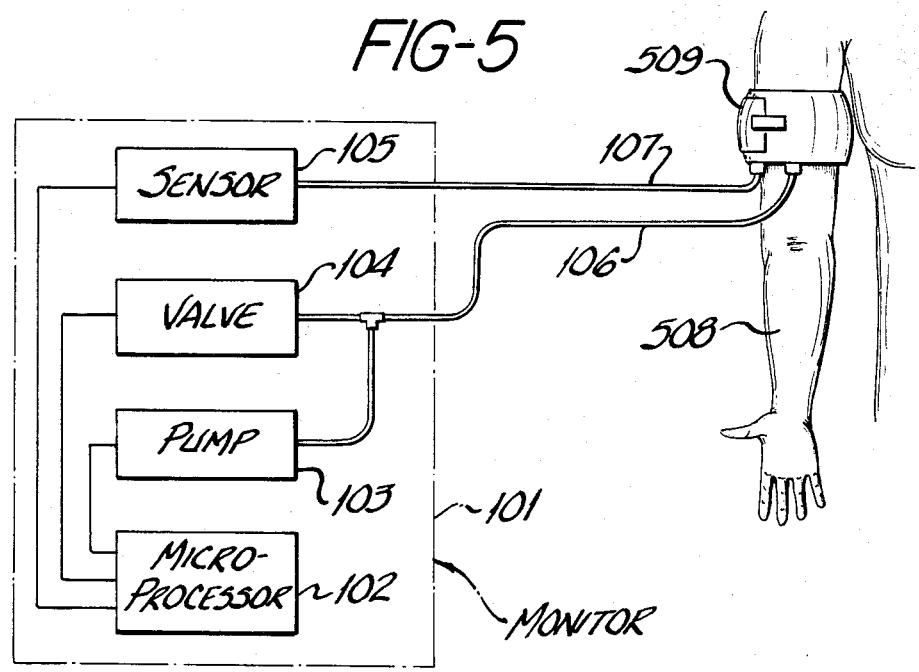
FIG-5
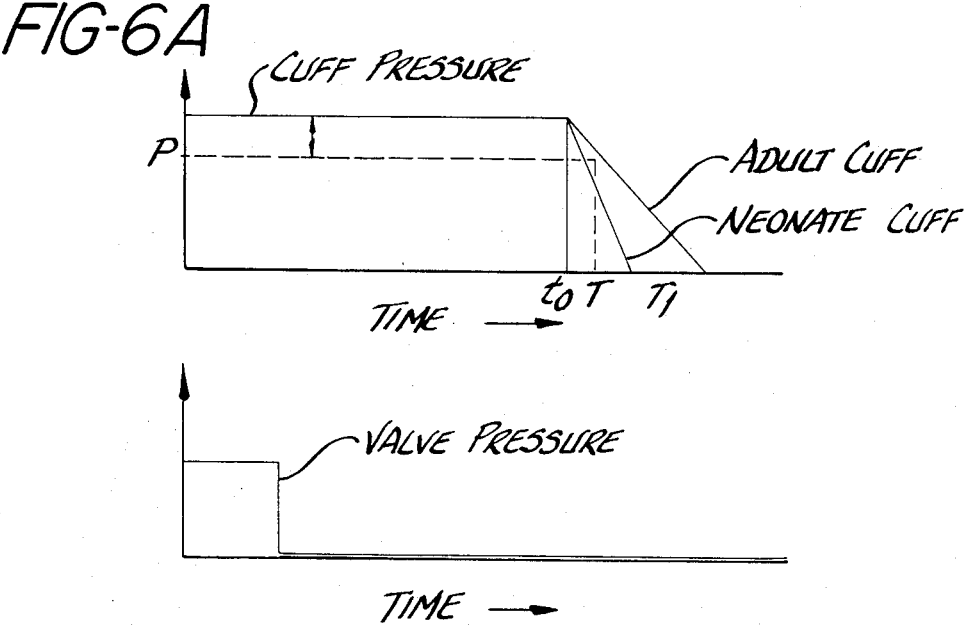
FIG-6A
FIG-6B even more clearly discriminated from one another.
AUTOMATIC IDENTIFICATION OF CUFF SIZE IN AUTOMATED BLOOD PRESSURE MONITORS

FIELD OF THE INVENTION

This invention relates to automated blood pressure monitoring, and more particularly to noninvasive automated monitors which utilize a selectively inflatable cuff to sense blood pressure.

BACKGROUND OF THE INVENTION

Automated blood pressure monitoring has become an indispensible tool in many aspects of medicine, perhaps the most important of which are those associated with the critical care patient. Increasingly, anesthesiologists utilize such monitors throughout surgical procedures, and the automated monitors are virtually universally used in critical care units, neonatal and adult intensive care units, and emergency treatment centers.

The most prevalent class of noninvasive blood pressure monitors utilize the so-called oscillometric method, and feature an inflatable cuff which is fitted over a limb of the patient, for example at the brachial artery. Through a complex system of inflation and/or deflation steps, the monitor senses arterial pressure changes and generates such information as mean arterial pressure, systolic pressure, diastolic pressure, and heart rate. Typically, the cuff size is adapted roughly to the anticipated arm size of the patients, and even though each typical cuff size permits some significant range of adjustability, the respective cuff sizes may be, on a volume basis, widely variant one from the other. Although given types of monitors operate with similar rationale regardless of the cuff size employed, it has been uncommon for any given unit to operate with more than one type or size of cuff and corresponding selective inflation volumes and pressures. Generally, this has been for the protection of neonates, who would be seriously injured if a cuff were to be inflated to the pressure levels required in the operation of sensing adult pressure. Hence, for the most part, commercial automated monitors have been designed to operate either for the neonate, or for adults, but not for both. Rarely, a given unit designed for both has been fitted with an operator actuated switch to select between neonatal and adult modes of operation; such units, however, have been regarded with considerable reluctance, since operator inadvertence could easily result in the application of the adult pressure parameters to the neonate.

It is a primary object of the present invention to provide methods and apparatus whereby automated blood pressure monitors may employ a variety of size ranges of cuffs, and which, automatically and without substantial dependence on operator diligence, will identify the type of blood pressure cuff actually to be utilized in the monitoring, and further will automatically adapt the system operating parameters to such type of cuff.

One prior art approach to such automated monitoring has been to measure the time required to inflate the cuff to a given pressure, or the time to inflate the cuff between two given pressures. In theory, the time required for such pumping is proportional to the volume of the cuff, and hence is indicative of the cuff size itself. In fact, however, artifacts resulting from line voltage changes, and variability of pump characteristics, often dominate the process, resulting in substantial rates of error in cuff identification. Another prior art approach has been to inflate the cuff to a given pressure, and then to measure the time required for a predetermined amount of deflation. Such an approach avoids artifacts caused by line voltage changes and pump variability, but encounters other difficulties. Specifically, any kinking in the hose or the cuff itself would result in substantial mischaracterization of cuff size. Indeed, such kinking is almost common in neonates, wherein the arm about which a cuff is applied is so small. Such kinking could easily prolong the deflation cycle, and cause an erroneous conclusion that the cuff volume is much larger than it is in fact.

It is a further object of the principles of the present invention to provide automated methods and apparatus for cuff identification which are substantially independent of line voltage changes and variability of pump characteristics, and which for neonates avoid errors caused by cuff blockages and kinking.

SUMMARY OF THE INVENTION

The principles of the present invention are premised upon measuring the time required for an audio pulse to propagate to, through, and back from the cuff, and discriminating cuff size based on that propagation time. That is, oscillometric blood pressure monitors which utilize inflation and/or deflation in order to measure blood pressure through changes in cuff pressure, conventionally entail a pump and valve at the monitor for inflating and/or deflating the cuff, and a pressure transducer, typically also at the monitor, which measures changes in cuff pressure. In point of fact, the pressure transducer acts, for purposes of audio pulses, as a microphone. Therefore, whether the cuffs are connected to the monitor by multiple lumens (i.e. loop), or by a single, bidirectional lumen, it is possible to generate an audio pulse at the pump/valve, which propagates out to and through the cuff and back to the transducer to be detected. Monitors typically include microprocessors and the like which are quite capable of monitoring these events, and calculating the time of propagation. Even if the tube length should be the same for neonatal and adult cuffs, the large differential in cuff volume between adult and neonatal cuffs engenders sufficient propagation differential for the monitor to discriminate between them. Typically, however, adult cuffs are connected to the monitor through tubing (e.g. 12 ft.) which is considerably longer than that utilized for neonatal cuffs (e.g. 6 or 8 ft.). For such typical cuffs which utilize different tube lengths, the acoustical propagation time differentials are further expanded, and respective cuffs may be In an illustrative embodiment, a microprocessor controlled oscillometric blood pressure monitor, such as the DINAMAP* brand monitor commercially available from Critikon, Inc., is provided with conventional adult and/or neonatal cuffs. The software control of such a unit is altered whereby, prior to execution of the blood pressure measurement routines, the cuff (then of unknown type) is inflated to a given pressure, whereupon the pressure control valve is released. There is thereby generated a pressure/acoustical pulse which propagates out through the cuff loop and back to the pressure transducer at the speed of sound. Such propagation is measured, and the measured propagation time is compared to a predetermined threshold intermediate the typical propagation times of neonatal and adult cuffs, respectively. The outcome of the comparison dictates which sort of cuff is attached, and based thereon, operational modes, including target inflation pressures and the like, are selected and executed. In an alternative embodiment, wherein typical adult and neonatal cuffs, having different tube loop lengths, are utilized, the neonatal cuff is provided with a shunt between respective tubes connecting the monitor to the cuff. Acoustical propagation in such instance is based predominantly on tube length, and the resulting differential is accentuated by the absence of a shunt across the larger volume adult cuff.

DESCRIPTION OF THE DRAWINGS

FIG. 3 shows a detailed isometric view of aspects relating to neonatal measurement;

FIG. 4 shows a partial cutaway of the embodiment of FIG. 3;

FIG. 5 shows an illustrative embodiment of the principles of the present invention, as applied to adult blood pressure monitoring; and FIGS. 6A and 6B show illustrative timing drawings whereby the principles of the present invention are gainfully employed for various monitoring applications.

BEST MODE OF CARRYING OUT THE INVENTION

Figure 1:
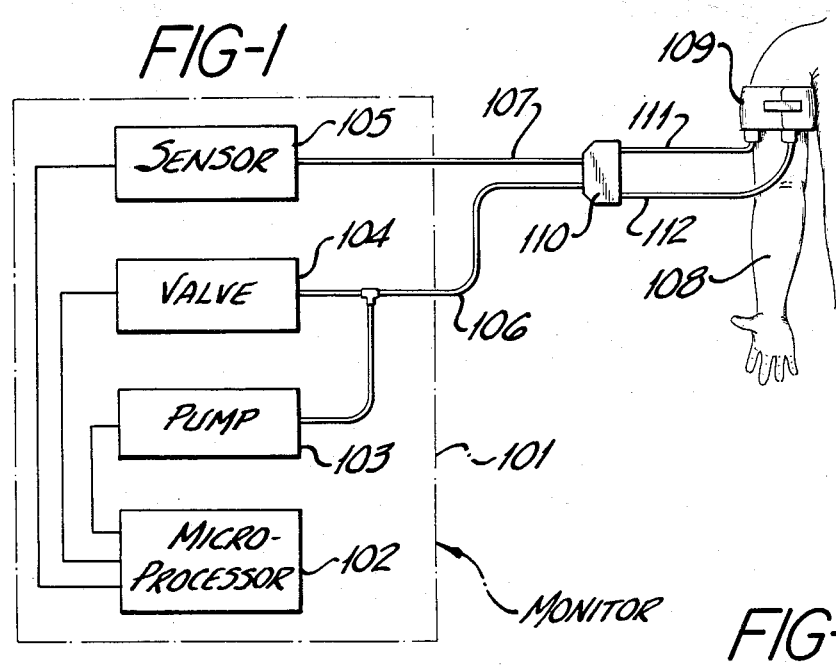
FIG. 1 shows an illustrative embodiment of the principles of the present invention, as applied to neonatal blood pressure monitoring.

In accordance with the principles of the present invention, substantially conventional, commercially available blood pressure monitoring apparatus may be suitably modified, as set forth herein, in order to practice the principles of the present invention without extensive experimentation. In particular, attention is called to a commercially available automated blood pressure monitor, known as the DINAMAP* brand unit, which is sold by Critikon, Inc., a company which is the assignee hereof and which has business offices at 1410 N. Westshore Blvd., Tampa, FL 33607, P.O. Box 22800, Tampa, FL 33622. The DINAMAP* brand blood pressure monitors are among the most popular and most extensively used units of their kind, enjoying a reputation for accuracy and reliability. The DINAMAP* brand monitors employ the oscillometric method of blood pressure determination, and utilize specially designed software in conjunction with a dedicated microprocessor for purposes of monitoring. Each unit has a monitor which includes a pump, a bleed valve, a pressure sensor, and a microprocessor. These workings are coupled through hoses to a cuff which is applied to the limb of the patient. Under control of the microprocessor, the cuff is inflated to a pressure known to be above systolic, and then is deflated in predetermined pressure decrements. At each such cuff pressure step, pressure fluctuations in the cuff, corresponding to those in the arm, are measured and subjected to a variety of processing criteria, with various artifact rejection schemes being employed at each step and among the steps. Heart rate, mean arterial pressure, systolic pressure, and diastolic pressure are measured and displayed. In certain modes, the pressure monitoring process is conducted periodically, with information gathered during a previous cycle being utilized to reduce the processing required at a given subsequent cycle.

Reference is had to U.S. Pat. Nos. 4,349,034, issued Sept. 14, 1982, and 4,360,029 issued Nov. 23, 1982, both to Maynard Ramsey, III, both entitled AUTOMATIC MEAN BLOOD PRESSURE READING DEVICE, and both hailing from common parentage. Both those patents describe relevant methods and apparatus for automatic blood pressure monitoring, including approaches to the rejection of artifacts in the measuring process. To the extent required to complete the disclosure hereof, both those patents are incorporated by reference herein.

Addtionally, reference is had to U.S. application Ser.No. 373,209, filed Apr. 29, 1982 in the names of Rush Hood and Richard Medero, assigned to the assignee hereof and entitled ADAPTIVE INCREMENTAL BLOOD PRESSURE MONITOR. That application describes a somewhat different blood pressure monitoring approach, wherein cuff pressure is optionally sequentially incremented, as well as decremented, for a more rapid evaluation of blood pressures. That application also describes apparatus and methods appropriate for automated blood pressure monitoring, and to the extent required to complete the disclosure hereof, that application is incorporated by reference herein.

Referring first to FIGS. 1 and 5, which show illustrative embodiments of the principles of the present invention as applied to neonates and adults, respectively, it will be appreciated that for some cases none, and at most minimal hardware changes need be made to commercially available apparatus, such as the DINAMAP* brand monitors, in order to practice the principles of the present invention. In both figures, a monitor 101 of conventional commercial pedigree includes a microprocessor 102 which controls, among others, a pump 103, a deflate valve 104, and a loop pressure sensor 105. As stated hereinabove, the microprocessor 102, understood to include associated software controls such as those resident in read only memory (ROM), establishes the monitoring sequence whereby the pump 103, with valve 104 closed, provides pressure to the loop and cuff via tubes 106 and 107. Thereupon, the valve 104 is periodically opened and shut, creating the pressure decrements in the cuff. At each such instance, the sensor 105 measures pressure in the cuff, which measurements are processed by the microprocessor 102, and in turn logical conclusions are derived concerning heart rate, mean arterial pressure, systolic pressure, and diastolic pressure.

In FIG. 1, a neonatal arm is provided with an appropriately sized cuff 109, for example which has a total volume in the range of 2 to 10 cc's. In FIG. 5, the adult arm 508 is provided with a cuff 509, which typically has volume in the range 20 to 350 cc. In either instance, it is the counterpressure of the cuff 109 or 509, against the arterial pressure in the arm which gives rise to pressure fluctuations at the sensor 105, and which in the aggregate may be processed to yield the desired data.

It will be noted that the neonatal apparatus of FIG. 1 further includes a shunt 110 across the tubes 106 and 107, which is applied for purposes of the principles of the present invention and which, through coupling of further tubes 111 and 112, allows the pump 103, valve 104, and sensor 105 to function in conventional fashion with the cuff 109 to evaluate blood pressure utilizing the oscillometric method. The structure and purpose of the shunt 110 are discussed more extensively hereinafter.

It will therefore be apparent, upon consideration of the embodiments of FIGS. 1 and 5, that for some applications of the principles of the present invention, no hardware adaptations need be made to the unit, and in neonatal case, a minor apparatus modification may be utilized.

Indeed, in preferred embodiments of the principles of the present invention, relatively minor software changes and additions, appropriately accomplished in the microprocessor 102 with its associated ROM's, will provide full beneficial use of the principles of the present invention. In fact, such software representation is the preferred approach to practice of the principles of the present invention. It will be understood, however, that those of ordinary skill may, depending upon various design constraints not relevant to the essentials of the invention, desire to utilize or configure special purpose hard-wired logic which accomplishes the principles of the present invention in like fashion. It is contemplated that the principles of the present invention do in fact embrace hard-wired, as well as software embodiments.

As stated hereinbefore, the principles of the present invention entail identification of blood pressure cuff size by measurement of acoustic propagation between the monitor and the cuff. With particular reference to FIG. 5, it is possible, through mechanism of a valve opening, to create an acoustical pulse which propagates through tube 106 to the cuff 109 or 509, through the cuff 109 or 509 and back into tube 107, to be detected by the sensor 105. That is, in conventional usage, the pressure sensor 105 has capacity also to function as a microphone, and indeed the acoustic pulse created by the valve 104 may be thought of as the leading edge of the pressure wave, which propagates through the system at the speed of sound. Thus, with particular reference to the embodiment of FIG. 5, the principles of the present invention may be practiced through operation of the pump 103, with valve 104 closed, to a predetermined level (under control of microprocessor 102), whereupon the valve 104 is open. At the time of opening, the microprocessor 102 commences a timing operation, which terminates when the acoustic pulse first generated by opening of the valve 104 propagates to the sensor 105.

Figure 2:
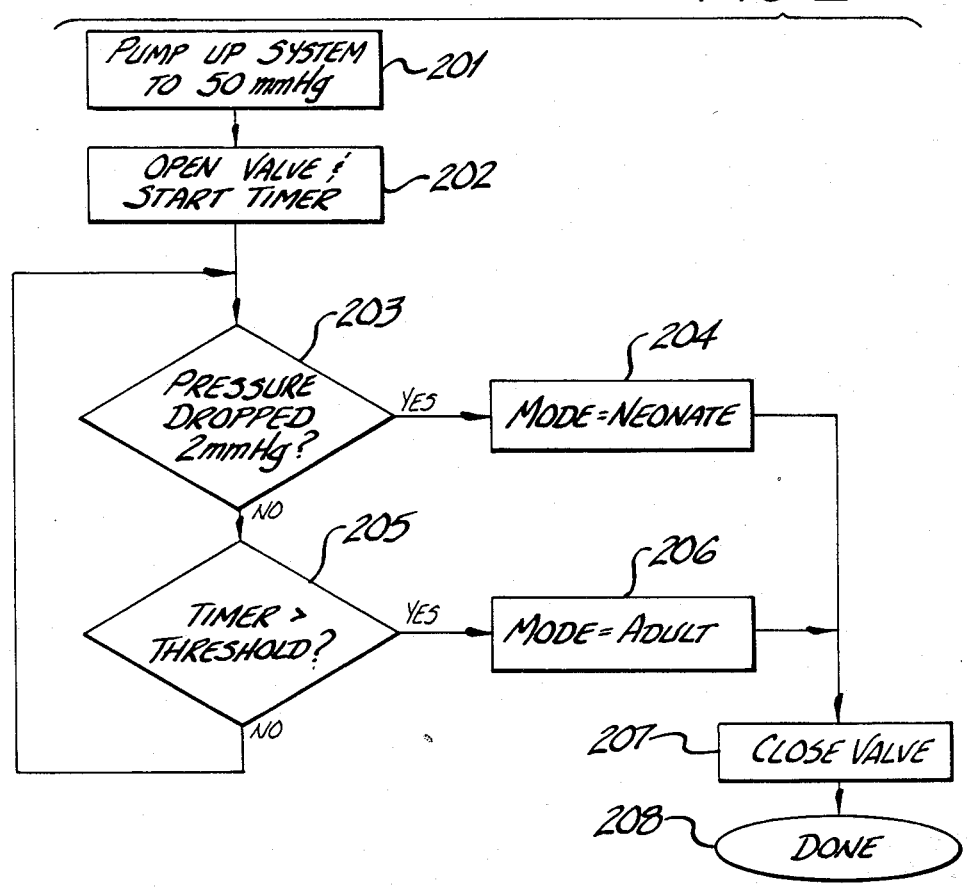
FIG. 2 shows a method embodying the principles of the present invention, in the form of a flow chart.

Referring next to FIG. 2, there is shown, in flow chart form, a preferred method of practicing the principles of the present invention. In particular, it is anticipated that the procedures of FIG. 2 may conveniently and without substantial experimentation be suitably coded and resident in the microprocessor 102, thereby to function for control of the pump 103, valve 104, and sensor 105, and together with various calculations in the microprocessor 102, to practice the principles of the present invention. It is anticipated that the procedures of FIG. 2 would at the least be performed at the initial operation of the system, to wit once the cuff 109 or 509 is applied to the arm of the patient, and before actual blood pressure measurements commence. It is also feasible, however, to practice the methods of FIG. 2 at any such time during the procedures as is deemed convenient or useful by the designer.

As shown in step 201, the system, that is the cuff 109 or 509, and the various tubes 106, 107, 111, and 112, are pumped up, by virtue of closure of valve 104 and operation of pump 103, to a predetermined threshold level, for example 50 millimeters of mercury. Thereupon, the valve 104 is opened, and simultaneously a timer resident in the microprocessor 102 is actuated. The opening of the valve 104 will cause a pressure or sound wave to propagate through the connecting tubes 106, 107, etc., and the cuff 109 or 509. Ignoring for the moment the shunt construction shown in FIG. 1 for neonates, in the normal course this sound wave will propagate from the valve 104 through tube 106 to the cuff, through the cuff and via tube 107 to the sensor 105.

As stated hereinbefore, the sensor 105 shares the physical attributes of a microphone, and hence the sensor 105 will register an electrical output signal to the microprocessor 102 at such a time as the sound wave, resulting from opening the valve 104, reaches the sensor 105. In general theory, it is the time between the opening of the valve 104, and the sensing thereof at 105, which is used to discriminate among ranges or types of blood pressure cuffs.

Referring again to FIG. 2, once the valve 104 is opened and the time is started, a loop is entered, constituted by repeated executions of decision steps 203 and 205. In particular, decision step 203 constitutes an ongoing monitoring, by the microprocessor 102, whether the pressure at sensor 105 has dropped by 2 millimeters mercury, that is, whether the sound wave from valve 104 has reached the sensor 105. The "no" branch of decision step 203 leads to the second aspect of the loop, a comparison at 205 whether the elapsed time is greater than a given threshold. Again, the "no" branch recirculates back to the decision step 203, and constitutes reconstitution of the loop.

The two exits from the loop, the "yes" results from both steps 203 and 205, indicate respective identification, at 204 and 206, that either a neonatal cuff or an adult cuff is being employed. The theory of the loop is that, initially of course the pressure will not have dropped, and indeed will not do so until the pressure wave from the open valve reaches the sensor 105. Thus, so long as the pressure has not dropped, and the loop is continually recirculating, the continuing passage of time will indicate that the valve pressure wave is still propagating through the system. As this recirculation of the loop continues, the elapsed time continues to increase, but so long as the elapsed time is below the given threshold, there is no basis to discriminate between adult and neonatal cuff sizes. In general, sound will propagate most rapidly (and indeed, below the threshold), in a system employing the neonatal cuff, and less rapidly in a system employing the adult cuff. Thus, to the extent that the timer ever exceeds the threshold, an adult cuff is indicated, the decision step 205 exits via the "yes" path, and the mode is indicated as adult at 206. The other exit from the loop would be if the pressure actually drops by 2 millimeters, indicating that the pressure front has propagated through the system from valve 104 to sensor 105, but has done so in a time less than that threshold of decision step 205. In such case, the loop will exit via "yes" branch of decision step 203, and the mode will be identified as neonatal at the step 204. In either event, once the mode is identified, the valve 104 is closed, indicated at step 207, and the cuff identification process is complete. The "done" step 28 simply indicates that the system is then conditioned for actual measurement of blood pressure, employing apparatus and routines suited for such purpose.

The operation of the methods set forth in FIG. 2 may perhaps be best understood upon consideration of the graphs of FIGS. 6A and 6B. In particular, noting first the waveform of FIG. 6A, there is shown the relative speeds of pressure relaxation, as a function of time, for cuffs of various size. That is, given that no cuff will deflate instantaneously (i.e., the step function downward at "$T_0$"), the rate of deflation is dependent on the volume of the cuff. Therefore, neonatal cuffs, being substantially smaller in volume, deflate more rapidly than adult cuffs. It is therefore clear that the threshold, or decision level at a given pressure "P", will allow for discrimination between the adult and neonate cuffs utilizing a threshold time "T". Comparing, therefore, the effect of a drop in valve pressure, shown in the FIG. 6B waveform, the timing threshold T necessary for the cuff to reach a given threshold P, or a threshold $T_1$ for complete deflation, will allow discrimination between the respective cuff sizes.

Given that cuff sizes such as adult and neonatal may be discriminated from one another in accordance with the principles of the present invention, simply based on deflation time, it is possible to enhance these results, and to increase reliability and decrease processing time, by utilization of a few optional expediencies. First, it is to be noted that in conventional usage, adult cuffs have longer tube leads (e.g. 12 ft.), whereas neonatal cuffs use substantially shorter tube leads (e.g. 6 to 8 ft.). This differential tends to accentuate the differences between neonatal and adult cuffs in accordance with the principles of the present invention.

Another method of accentuating the difference between sizes in accordance with the principles of the present invention is to utilize a shunt for the smaller size. With particular reference to FIGS. 3 and 4, there is shown a preferred version of such a shunt. In particular, FIG. 3 shows an isometric drawing of the pressure circuit employed in FIG. 1, and FIG. 4 shows a partial cutaway of that apparatus, particularly the shunt module 110.

In FIGS. 3 and 4, the shunt 110 provides a channel 401 which interconnects the tube 106 from the valve, with the tube 107 to the sensor. Likewise, via openings 403 and 405 and connectors 406 and 407, it shunts the inflatable bladder of the cuff 109. A set screw 412 allows the shunt to be opened for cleaning and the like.

In operation, the shunt 110 does have an effect for transient signals in the pressure line, such as the propagating pressure front which is utilized in accordance with the principles of the present invention, but is of sufficiently small volume as to have no substantial effect on the steady state operations which occur at pressure intervals through the cycle. That is, once the system stabilizes at each cuff pressure decrement at which oscillometric blood pressure procedures are followed, the low volume of the channel 401 prevents any consequent effect on the accuracy of readings at the sensor 105.

In practice, the shunt 110, especially when utilized in a shorter neonatal circuit, provides a substantial speed and processing advantage in the discrimination between respective cuff sizes. It will be noted that shunts could be employed in various other discrimination schemes, for example to accentuate the difference between two cuff sizes which are quite similar in volume to one another.

It will be appreciated that the foregoing sets forth preferred and illustrative embodiments of the principles of the present invention, but that numerous alternative embodiments will occur to those of ordinary skill in the art without departure from the spirit or the scope of the principles of the present invention. For example, although the preferred embodiments set forth herein are adapted simply to discriminate between neonatal and adult cuff sizes, the same principles could gainfully and easily be extended to discriminate among several alternative sizes or classes of cuff, simply by employing multiple thresholds in the procedure of FIG. 2. Likewise, variation of sizes of the tubes interconnecting the monitor with the cuffs, can be utilized to accentuate the differentials which would otherwise exist. Further, variation of location of the shunt along the path could be utilized for further accentuation of the discrimination scheme.

I claim:

1. In an automatic blood pressure monitoring system for monitoring both neonatal and adult patients with a single monitor, a method of automatically detecting use of a neonatal cuff comprising the steps of:
   (a) inflating said cuff to a predetermined pressure;
   (b) coupling an acoustic pulse from said monitor to said cuff;
   (c) detecting return of said acoustic pulse to said monitor from said cuff;
   (d) measuring the time duration of propagation of said pulse;
   (e) comparing said measured duration with a predetermined reference threshold; and
   (f) commencing neonatal monitoring if said measured duration has a predetermined relationship with said threshold.

2. In a blood pressure monitoring system employing a selectively inflatable cuff interconnected in a pressurized closed loop with a monitoring system, said system including a transducer for measuring loop pressure, a method for identifying the one of a selection of cuffs which is connected to the monitor, comprising the steps of:
   (a) inflating said cuff to a predetermined pressure;
   (b) creating a pressure change pulse at a portion of said loop opposite said transducer with respect to said cuff;
   (c) detecting said pulse at said transducer; and
   (d) measuring the time duration between creation of said pulse and detection thereof; said time duration being associated in predetermined fashion with one of said cuffs.

3. In an automated blood pressure monitoring system, a method for automatically determining which one of a select class of cuffs are to be empolyed, comprising the steps of:
   (a) inflating said cuff to a predetermined pressure;
   (b) establishing a target pressure which is different from said predetermined pressure;
   (c) changing the cuff pressure at a given rate in the direction of said target pressure; and
   (d) measuring the time required to reach said target pressure, said measured time being indicative of which cuff is to be employed in the system.

* * * * *